United States Patent
Callaghan et al.

(10) Patent No.: US 7,208,012 B2
(45) Date of Patent: Apr. 24, 2007

(54) COVALENTLY-BOUND, HYDROPHILIC COATING COMPOSITIONS FOR SURGICAL IMPLANTS

(75) Inventors: Thomas A. Callaghan, Fort Worth, TX (US); Albert R. LeBoeuf, Burleson, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 11/550,938

(22) Filed: Oct. 19, 2006

(65) Prior Publication Data

US 2007/0043436 A1 Feb. 22, 2007

Related U.S. Application Data

(62) Division of application No. 10/917,773, filed on Aug. 13, 2004, now Pat. No. 7,157,538.

(51) Int. Cl.
*A61F 2/16* (2006.01)
(52) U.S. Cl. .................. 623/6.62; 623/6.11; 428/64.1; 428/476.3; 428/515
(58) Field of Classification Search .............. 428/64.1, 428/515, 476.3; 623/6.62, 6.11
See application file for complete search history.

(56) References Cited

U.S. PATENT DOCUMENTS

| 4,578,504 A | 3/1986 | Hammar ..................... 560/112 |
| 4,638,040 A | 1/1987 | Hammar ..................... 526/245 |
| 4,673,539 A | 6/1987 | Hammar et al. ............. 264/1.1 |
| 4,786,446 A | 11/1988 | Hammar et al. ............. 264/2.6 |
| 4,921,884 A | 5/1990 | Hammer et al. ............ 523/106 |
| 5,002,792 A | 3/1991 | Vegoe ........................... 427/2 |
| 5,094,876 A | 3/1992 | Goldberg et al. .............. 427/2 |
| 5,108,776 A | 4/1992 | Goldberg et al. .............. 427/2 |
| 5,130,160 A | 7/1992 | Goldberg et al. .............. 427/2 |
| 5,152,787 A | 10/1992 | Hamblen ....................... 623/6 |
| 5,290,548 A | 3/1994 | Goldberg et al. ........ 424/78.18 |
| 5,290,892 A | 3/1994 | Namdaran et al. .......... 526/259 |
| 5,554,187 A | 9/1996 | Rizzo, III ...................... 623/6 |
| 5,603,774 A | 2/1997 | LeBoeuf et al. ............... 134/1 |
| 5,888,243 A | 3/1999 | Silverstrini .................... 623/5 |
| 6,388,035 B1 | 5/2002 | LeBoeuf ..................... 526/264 |
| 6,528,602 B1 | 3/2003 | Freeman et al. ........... 526/259 |

FOREIGN PATENT DOCUMENTS

| EP | 0 559 820 B1 | 2/1998 |
| EP | 0 908 476 A2 | 4/1999 |
| JP | 11056999 A | 3/1999 |
| WO | WO 95/11279 | 4/1995 |
| WO | WO 96/40303 | 12/1996 |
| WO | 99/11303 A1 | 3/1999 |
| WO | WO 99/52570 | 10/1999 |
| WO | WO 00/34804 | 6/2000 |

OTHER PUBLICATIONS

Brook, "Thermoplastic Hydrogels," *British Polymer Journal*, vol. 23, pp. 257-259 (1990).
Capozza et al., "Advanced in Thermoplastic Hydrogels," *Polymer Preprints*, vol. 31(2), p. 57 (1990).
Carbutt, "A Novel Thermoplastic Hydrogel," Master Thesis submitted at University of Lowell (1983).
Liu et al., "Preparation and Characterization of Some Linear Copolymers as Precursors to Thermoplastic Hydrogels," *Eur. Polym. J.*, vol. 30(4), pp. 457-463 (1994).
Nasar et al., "Synthesis and Properties of Imidazole-Blocked Diisocyanates," *Polymer International*, vol. 48, pp. 614-620 (1999).
Regulski et al., "Isocyanatoethyl Methacrylate II: The Blocked Isocyanate Derivatives, Preparation and Deblocking," *ACS Organic Coatings & Applied Polymer Science Proceedings*, vol. 48, p. 998 (1983).
Regulski et al., "Isocyantoethyl Methacrylate III: Polymerization, Formulation and Evaluation of Blocked IEM Derivatives," *ACS Organic Coatings & Applied Polymers Science Proceedings*, vol. 48, pp. 1003-1007 (1983).

*Primary Examiner*—Alexander S. Thomas
(74) *Attorney, Agent, or Firm*—Patrick M. Ryan

(57) ABSTRACT

Covalently-bound, hydrophilic copolymer coatings for implants are disclosed. The copolymer coatings comprise a hydrophobic aryl acrylic monomer, a hydrophilic monomer selected from the group consisting of hydroxyalkyl (meth) acrylates, n-vinyl pyrrolidone and acrylamides, and a (meth) acrylamide reactive plasticizer.

7 Claims, No Drawings

COVALENTLY-BOUND, HYDROPHILIC COATING COMPOSITIONS FOR SURGICAL IMPLANTS

This application is a divisional application of U.S. Ser. No. 10/917,773, filed Aug. 13, 2004, now U.S. Pat. No. 7,157,538.

FIELD OF THE INVENTION

This invention relates to coatings for surgical implants. In particular, the present invention relates to hydrophilic, covalently cross-linked copolymers that are covalently bound to the surface of surgical implants.

BACKGROUND OF THE INVENTION

Both rigid and foldable implantable ophthalmic lens materials are known. The most common rigid material used in ophthalmic implants is polymethyl methacrylate ("PMMA"). Foldable intraocular lens ("IOL") materials can generally be divided into three categories: silicone materials, hydrogel materials, and non-hydrogel ("hydrophobic") acrylic materials. See, for example, *Foldable Intraocular Lenses*, Ed. Martin et al., Slack Incorporated, Thorofare, N.J. (1993). For purposes of the present application, hydrophobic acrylic materials are acrylic materials that absorb less than approximately 5% water at room temperature.

Silicone and non-hydrogel acrylic materials used in ophthalmic implants can potentially damage endothelial cells and perhaps other cells or tissues as well during or after the implant's insertion in the eye. These materials are generally hydrophobic and/or tacky and can pull cells off of eye tissues that contact the implant. Particularly in the case of phakic IOL's implanted between the capsular bag and the iris, there is significant potential for physical contact between the implant and surrounding cells or tissue even after the implant reaches its target location.

SUMMARY OF THE INVENTION

The present invention relates to hydrophilic coating compositions for surgical implants, particularly ophthalmic implants comprising silicone, hydrophobic acrylic or hydrogel materials. More specifically, the present invention relates to a copolymeric coating material for an implant where the copolymeric coating material is capable of absorbing from at least 5 to about 90% water and comprises
(i) a hydrophobic aryl acrylic monomer of formula (I)

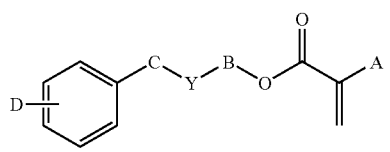

wherein: A is H, $CH_3$, $CH_2CH_3$, or $CH_2OH$;
B is $(CH_2)_m$ or $[O(CH_2)_2]_n$;
C is $(CH_2)_w$;
m is 2–6;
n is 1–10;
Y is nothing, O, S, or NR, provided that if Y is O, S, or NR, then B is $(CH_2)_m$;

R is H, $CH_3$, $C_nH_{2n+1}$ (n=1–10), iso-$OC_3H_7$, $C_6H_5$, or $CH_2C_6H_5$;
w is 0–6, provided that m+w≦8; and
D is H, $C_1$–$C_4$ alkyl, $C_1$–$C_4$ alkoxy, $C_6H_5$, $CH_2C_6H_5$ or halogen;
(ii) a hydrophilic monomer selected from the group consisting of hydroxyalkyl (meth)acrylates; n-vinyl pyrrolidone and acrylamides; and
(iii) a reactive plasticizer of the formula

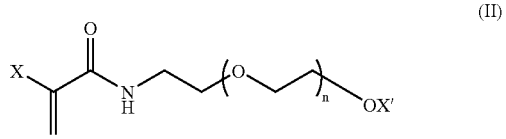

wherein: X and X' are independently H, $CH_3$, $CH_2CH_3$, $CH_2CH_2CH_3$, $CH_2OH$, or $CH_2CH_2OH$; and
n is 3–113, such that the average molecular weight of the polyethylene glycol unit is 132–5000.

The present invention also relates to methods for applying the copolymeric coating material as specified above to an implant's surface. In one embodiment, the method comprises dissolving the copolymer containing a latent cross-linking agent in a solvent to form a coating solution, contacting the coating solution with the implant's surface, and activating the latent cross-linking agent in the coating copolymer. In another embodiment, the method comprises dissolving the copolymer in a solvent to form a coating solution, adding a cross-linking agent to the coating solution, contacting the coating solution with the implant's surface, and heating the coated implant to generate cross-linking.

DETAILED DESCRIPTION OF THE INVENTION

Unless indicated otherwise, all amounts are expressed as weight %.

The coating material of the present invention is a copolymer comprising:
(i) a hydrophobic aryl acrylic monomer of formula (I);
(ii) a hydrophilic monomer selected from the group consisting of hydroxyalkyl (meth)acrylates; n-vinyl pyrrolidone and acrylamides; and
(iii) a reactive plasticizer of formula (II).

Preferred aryl acrylic monomers of formula (I) for use in the coating materials of the present invention are those wherein A is $CH_3$, B is $(CH_2)_m$, m is 2–5, Y is nothing or O, w is 0–1, and D is H. Most preferred monomers of formula (I) are 2-phenylethyl methacrylate ("2-PEMA"); 3-phenylpropyl methacrylate; 4-phenylbutyl methacrylate; 5-phenylpentyl methacrylate; 2-benzyloxyethyl methacrylate; and 3-benzyloxypropyl methacrylate.

Monomers of structure (I) are known and can be made by known methods. For example, the conjugate alcohol of the desired monomer can be combined in a reaction vessel with methyl methacrylate, tetrabutyl titanate (catalyst), and a polymerization inhibitor such as 4-benzyloxy phenol. The vessel can then be heated to facilitate the reaction and distill off the reaction by-products to drive the reaction to completion. Alternative synthesis schemes involve adding methacrylic acid to the conjugate alcohol and catalyzing with a carbodiimide or mixing the conjugate alcohol with methacryloyl chloride and a base such as pyridine or triethylamine.

The coating material contains an aryl acrylic monomer of formula (I) in an amount generally ranging from 10–60%, and preferably ranging from 20–50%.

The coating material contains an amount of hydrophilic monomer (separate from the reactive plasticizer ingredient described below) generally ranging from 5–70%. Suitable acrylamides include methacrylamide, ethacrylamide and propacrylamide as well as alkyl and aryl substituted acrylamides, such as dimethyl (meth)acrylamide; diethyl (meth)acrylamide and dipropyl (meth)acrylamide. Suitable hydrophilic monomers for use in the coating material also include hydroxyalkyl (meth)acrylates and n-vinyl pyrrolidone ("NVP"). Suitable hydroxyalkyl (meth)acrylates include 2-hydroxyethyl methacrylate; 1,3-dihydroxypropyl methacrylate; 2,3-dihydroxypropyl methacrylate; mixtures of 1,3- and 2,3-dihydroxypropyl methacrylate ("GMMA"); and monomethoxy glyceryl methacrylate. Mixtures of two or more hydrophilic monomers are also permitted. The most preferred hydrophilic monomer for use in the coating materials of the present invention are hydroxyethyl methacrylamide ("HEMAM") and aminopropyl methacrylamide ("APMAM").

Suitable reactive plasticizers or softening agents are those of formula (II). Preferred are those wherein X' is H or $CH_3$. These ingredients can reduce or minimize haze or crazing. The most preferred plasticizer is polyethylene glycol (400) monomethylether monomethacrylamide. The amount of the reactive plasticizer will range generally from about 20 to about 40%. Depending on the implant's function and the thickness of the coating, some degree of haze or crazing may be tolerated such that large amounts of the reactive plasticizer may not be required.

The coating material is capable of absorbing from at least 5 to about 90% water, and preferably from about 30 to about 80% water. The proportion of the copolymer's monomers will depend on the desired water content. In a most preferred embodiment, the desired water content is about 40 to about 60% and the coating material comprises from 20 to 50% of a monomer of formula (I), from 5 to 20% of hydroxyethyl methacrylamide or aminopropyl methacrylamide, from 0 to 40% of NVP and from 20 to 40% of a reactive plasticizer of formula (II).

In one embodiment, in addition to the ingredients described above, the coating material also comprises a latent cross-linking agent, such as a blocked isocyanate. Suitable blocked isocyanate compounds include imidazole blocked isocyanatoethyl methacrylate and imidazole blocked isocyanatoethyl methacrylamide. In this embodiment, the latent cross-linking agent is copolymerized with the other ingredients of the coating copolymer. In an alternative embodiment, the cross-linking agent is not added until the point where the coating copolymer is dissolved to form a coating solution. Examples of cross-linking agents that are suitable for use in this alternative embodiment include di-imidazole blocked 1,12-isocyanatododecane and peroxides, such as benzoyl peroxide and 2,4-dichlorobenzoyl peroxide.

The amount of the cross-linking agent contained in the coating compositions of the present invention will depend upon, among other factors, the chosen cross-linking agent and the degree of cross-linking desired. In general, the amount of the cross-linking agent necessary to cross-link the coating composition and secure it to the implant's surface will be about 0.5–4% for blocked isocyanates and about 3–6% for peroxides.

The copolymeric coating material is prepared by combining the chosen monomer of formula (I), hydrophilic monomer, reactive plasticizer, and a polymerization initiator (optionally with a latent cross-linking agent) to form a coating composition and then curing the coating composition. Any type of polymerization initiator may be used, including thermal initiators and photoinitiators, provided that the initiator can be activated without activating the latent cross-linking agent if present. Preferred initiators are UV- and blue-light activated initiators. The most preferred initiator is the benzoylphosphine oxide initiator, 2,4,6-trimethyl-benzoyldiphenylophosphine oxide ("TPO"), which is activated by blue-light. The amount of the polymerization initiator in the coating compositions of the present invention will depend upon the curing conditions. In general, however, the amount will be about 3% (w/w) or less, preferably about 2% (w/w) or less, and most preferably about 1% (w/w).

In order to prevent premature cross-linking, the coating compositions of the present invention do not contain significant amounts of monomers having more than one unsaturated bond. Such ingredients include the common cross-linking monomers ethyleneglycol dimethacrylate; diethylene glycol dimethacrylate; ethyleneglycol diacrylate; allyl methacrylates; allyl acrylates; 1,3-propanediol dimethacrylate; 1,6-hexanediol dimethacrylate; 1,4-butanediol dimethacrylate; polyethyleneoxide diacrylates; and the like.

In addition to the monomer of formula (I), hydrophilic monomer, plasticizer, any latent cross-linking agent, and polymerization initiator, the coating compositions optionally include one or more ingredients selected from the group consisting of UV absorbers that are copolymerizable with the monomer of formula (I), hydrophilic monomer and reactive plasticizer; blue-light blocking colorants that are copolymerizable with the monomer of formula (I), hydrophilic monomer and reactive plasticizer; and chain transfer agents to retard cross-linking within the coating copolymer.

Ultraviolet absorbing chromophores can be any compound which absorbs light having a wavelength shorter than about 400 nm, but does not absorb any substantial amount of visible light. Suitable copolymerizable ultraviolet absorbing compounds are the substituted 2-hydroxybenzophenones disclosed in U.S. Pat. No. 4,304,895 and the 2-hydroxy-5-acryloxyphenyl-2H-benzotriazoles disclosed in U.S. Pat. No. 4,528,311. The most preferred ultraviolet absorbing compound is 2-(3'-methallyl-2'-hydroxy-5'-methyl phenyl) benzotriazole. Suitable polymerizable blue-light blocking chromophores include those disclosed in U.S. Pat. No. 5,470,932. If a blue-light activated polymerization initiator is chosen and a blue-light blocking colorant is added, the polymerization initiator identity or concentration may have to be adjusted to minimize any interference.

The chain transfer agent, if present, is typically added in an amount ranging from 0.01 to 1.0%. Many chain transfer agents are known in the art. Examples of suitable chain transfer agents include 1-dodecanethiol and 2-mercaptoethanol.

After the coating copolymer is polymerized, a coating solution is prepared by dissolving the coating copolymer in a solvent or mixture of solvents, such as a 50:50 (parts by weight) mixture of ethanol and 2-pentanone or a 50:50 (parts by weight) mixture of ethanol and methyl propionate. The solvent or mixture of solvents is preferably chosen to give a clear, homogenous coating solution where the chosen solvent or solvent mixture does not evaporate so quickly that it leaves a hazy coating. If no latent cross-linking agent was included in the coating copolymer, a cross-linking agent, such as di-imidazole blocked 1,12-isocyanatododecane or a peroxide, is added to the coating solution.

The concentration of the coating copolymer in the coating solution will depend on the desired coating thickness. Other factors that will influence the thickness of the coating include the viscosity of the coating solution, the temperature of the coating solution and the implant, and the evaporation rate of the chosen solvent(s). In general, the coatings of the present invention will be no more than 1 µm thick, and preferably will be about 0.5 µm thick. A minimum coating thickness of about 0.01 µm is likely necessary to allow the coating to survive any manipulation of the implant (such as the folding of an IOL) and any abrasion caused during implantation or extended residence at the target site in a patient. A concentration of coating copolymer of about 7–9% in the coating solution will typically produce a coating about 0.5 µm thick in a dip-coating process.

The coating solution is applied to the implant by conventional techniques, such as spin- or dip-coating processes. Dip-coating is preferred. The implant is preferably dipped quickly so as to minimize any swelling of the implant caused by the solvent in the coating solution.

After the coating is applied to the implant, the coating is dried. A two-stage drying process is preferred. First, the coated implant is allowed to dry in air until most or all of the solvent has evaporated (generally ≦15 minutes). Second, the coated implant is baked at elevated temperature, about 80–110° C., to eliminate as much of the remaining solvent as possible and to activate the cross-linking agent. A preferred drying process involves room temperature air drying for 15 minutes, followed by baking at 110° C. for about 2 hours for blocked isocyanate cross-linking agents and 110° C. for about 3–5 hours for peroxide cross-linking agents.

Once the coating is secured to the implant's surface by covalent bonds formed by activating the cross-linking agent, the coating cannot be removed by solvents or solvent mixtures, including the same solvent used as the base in the preparation of the coating solution. After the coating is covalently-bound to the implant's surface, any impurities or unbound ingredients in the coating (or implant) may be removed by extraction in a suitable solvent, such as acetone in the case where the implant is an ACRYSOF® IOL. It is important that the swell response of the coating and the substrate to the extraction solvent not be too different in order to prevent damage to one or both during the extraction process. To prevent crazing or cracking of the coating, the swell of the coating should be greater than or equal to that of the substrate.

Before the coated implant is manipulated, the coating is preferably hydrated for several seconds to minimize crazing or other damage to the coating.

The implants suitable for coating with the hydrophilic coatings of the present invention are preferably made of hydrophobic acrylic materials, but could also be constructed of silicone, silicone-acrylic copolymers or hydrogels. The coating material should be selected so that it is not identical to the implant or "substrate" material that is to be coated. Additionally, the coating material should be selected so that it is capable of absorbing a greater amount of water (i.e, a higher water content material) than the substrate material. Preferred implant or substrate materials include the acrylic materials described in U.S. Pat. Nos. 5,290,892 and 5,693,095, the entire contents of which are hereby incorporated by reference. In the case where the implant is an IOL, the coatings of the present invention may be used in conjunction with substrate materials intended for use as a "hard" IOL (that is inserted in an unfolded state) or a "foldable" or "soft" IOL (that is inserted in a folded or compressed state). For example, the IOL material to be coated could be those IOL materials disclosed in U.S. Pat. Nos. 5,693,095 or 5,331,073. The coating may be applied to the entire IOL or to only a portion of the IOL. As used herein, "implants" includes contact lenses.

In order to prepare the implant material to be coated so that it is capable of receiving the coating, it may be necessary or desirable to expose the surface to be coated to a plasma gas prior to applying the coating composition of the present invention. Suitable plasma gases include argon, allyl amine, ethylene diamine, diallyl amine, and oxidizing gases, such as oxygen gas. A suitable plasma chamber is the P²CIM B-Series plasma chamber made by Advanced Plasma Systems, Inc. Using such a chamber, suitable plasma parameters include: power=400 W, plasma gas=oxygen; pressure of the plasma gas=225 mTorr; exposure time=4–6 minutes.

The following examples are intended to be illustrative but not limiting.

EXAMPLES 1–3

(Latent Cross-linking Agent):

The formulations shown in Table 1 below can be prepared and cured in polypropylene slab molds (10 mm×20 mm×0.9 mm). The formulations can be cured by exposure to blue light for one hour using a Kulzer Palatray CU blue light unit (12–14 mW/cm²).

Coating Solution Preparation

The coating copolymer of Examples 1–4 can be dissolved in a 49:49:2 pbw ethanol:methyl propionate:methylene chloride solvent to give a 6% solution. The resulting solutions can be filtered through a Gelman glass fiber Acrodisc (1 µm) to give particulate-free coating solutions.

Substrate

A copolymer comprising 65% 2-phenylethyl acrylate; 30% 2-phenylethyl methacrylate; 1.8% o-methyl Tinuvin P; and 3.2% 1,4-butanediol diacrylate can be prepared using 1.8% Perkadox-16 as a thermal initiator. This copolymer, cured in the slab molds described above, extracted in acetone for approximately 2 hours, dried in air at room temperature for about 1 hour, and then dried in an oven at 100° C. for about 1 hour is prepared. This material in the form of the defined slabs served as the implant/substrate material for all Examples ("the implant slabs").

The implant slabs for Examples 1–4 are treated with an allyl amine plasma for 2 minutes using a power of 200 W and a plasma gas pressure of 100 mTorr.

Coating Application

The implant slabs are dipped in the coating solutions. Caution is taken to minimize the immersion time of the samples in the coating solution as the solvent will swell the sample. The coated implant is allowed to dry in air at room temperature for 15 minutes, followed by baking at 100–110° C. for 1.5–2 hours to activate the latent cross-linking agent and secure the coating to the implant slab's surface.

TABLE 1

Coating Material
(all amounts in parts by weight)

| INGREDIENT | Ex. 1 | Ex. 2 | Ex. 3 |
|---|---|---|---|
| 2-PEMA | 22.8 | 30 | 39.6 |
| APMAM | — | 20 | 10 |
| HEMAM | 35 | — | — |
| NVP | 10 | 18 | 18 |
| PEG (400) Monomethylether Monomethacrylamide | 30 | 30 | 29 |

TABLE 1-continued

| | Coating Material (all amounts in parts by weight) | | |
|---|---|---|---|
| INGREDIENT | Ex. 1 | Ex. 2 | Ex. 3 |
| Imidazole Blocked Isocyanatoethyl Methacrylamide | 1.0 | 1.0 | 2 |
| 1-Dodecanethiol | 0.4 | 0.2 | 0.4 |
| Lucirin TPO | 0.8 | 0.8 | 1 |

Example 4

(Cross-Linking Agent Added When Coating Solution is Formed):

Coated implant slabs are prepared according to the procedure described above for Examples 1–3 except that the coating material contains the ingredients shown in Table 2 below. The coating copolymer is cured using the Kulzer Palatray CU unit for one hour. A coating solution is formed by dissolving the coating copolymer in a 50:50 methyl propionate:ethanol solvent to form an 8.0% solution. The implant slabs are dip coated and allowed to dry in air at room temperature for 15 minutes, followed by baking at 110° C. for 2 hours to de-block the isocyanate cross-linking agent and secure the coating to the implant's surface.

TABLE 2

| (all amounts in parts by weight) | |
|---|---|
| INGREDIENT | Ex. 4 |
| 2-PEMA | 32.9 |
| APMAM | 35 |
| PEG (400) Monomethylether Monomethacrylamide | 30 |
| di-Imidazole Blocked 1,12-diisocyanatododecane | 1.0 |
| 1-Dodecanethiol | 0.30 |
| Lucirin TPO | 0.80 |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A coated surgical implant comprising a coating and a substrate wherein the coating and the substrate are not identical, the coating is attached to the substrate by covalent bonds, the coating is from about 0.01 to about 1 μm thick, and the coating comprises a covalently cross-linked copolymer comprising (i) a hydrophobic aryl acrylic monomer of the formula

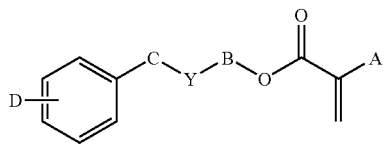

wherein: A is H, $CH_3$, $CH_2CH_3$, or $CH_2OH$;
B is $(CH_2)_m$ or $[O(CH_2)_2]_n$;
C is $(CH_2)_w$;
m is 2–6;
n is 1–10;
Y is nothing, O, S, or NR, provided that if Y is O, S, or NR, then B is $(CH_2)_m$;
R is H, $CH_3$, $C_nH_{2n+1}$ (n=1–10), iso-$OC_3H_7$, $C_6H_5$, or $CH_2C_6H_5$;
w is 0–6, provided that m+w≦8; and
D is H, $C_1$–$C_4$ alkyl, $C_1$–$C_4$ alkoxy, $C_6H_5$, $CH_2C_6H_5$ or halogen;

(ii) a hydrophilic monomer selected from the group consisting of hydroxyalkyl (meth)acrylates; n-vinyl pyrrolidone and acrylamides;

(iii) a reactive plasticizer of the formula

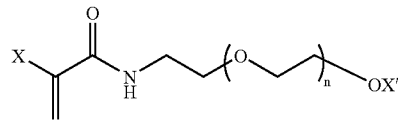

wherein: X and X' are independently H, $CH_3$, $CH_2CH_3$, $CH_2CH_2CH_3$, $CH_2OH$, or $CH_2CH_2OH$; and
n is 3–114, such that the average molecular weight of the polyethylene glycol unit is 132–5000;
and a cross-linking agent, and wherein the covalently cross-linked copolymer is capable of absorbing from at least 5 to about 90% water.

2. The coated surgical implant of claim 1 wherein the substrate comprises a hydrophobic acrylic material.

3. The coated surgical implant of claim 1 wherein the covalently cross-linked copolymer comprises a hydrophilic monomer selected from the group consisting of acrylamides.

4. The coated surgical implant of claim 3 wherein the acrylamide is selected from the group consisting of hydroxyethyl methacrylamide and aminopropyl methacrylamide.

5. The coated surgical implant of claim 1 wherein the covalently cross-linked copolymer is capable of absorbing from about 30 to about 80% water.

6. The coated surgical implant of claim 1 wherein the covalently cross-linked copolymer comprises from about 10–60% of the hydrophobic aryl acrylic monomer, from about 5–70% of hydrophilic monomer and from about 20–40% of reactive plasticizer, and wherein the reactive plasticizer is polyethylene glycol (400) monomethylether monomethacrylamide.

7. The coated surgical implant of claim 3 wherein the implant is selected from the group consisting of intraocular lenses and contact lenses.

* * * * *